(12) United States Patent
Dewey

(10) Patent No.: US 7,922,749 B2
(45) Date of Patent: Apr. 12, 2011

(54) REDUCING DEVICE

(75) Inventor: Jonathan Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 11/404,212

(22) Filed: Apr. 14, 2006

(65) Prior Publication Data

US 2007/0270811 A1 Nov. 22, 2007

(51) Int. Cl.
*A61B 17/88* (2006.01)

(52) U.S. Cl. .......................... 606/279; 606/246

(58) Field of Classification Search .......... 606/246–248, 606/251–253, 262, 267, 270–272, 275, 104, 606/279
See application file for complete search history.

(56) References Cited

U.S. PATENT DOCUMENTS

| | | | |
|---|---|---|---|
| 5,154,719 A * | 10/1992 | Cotrel | ........................ 606/308 |
| 5,217,497 A | 6/1993 | Mehdian | |
| 5,474,555 A | 12/1995 | Puno | |
| 5,545,165 A * | 8/1996 | Biedermann et al. | ......... 606/261 |
| 5,554,157 A | 9/1996 | Errico | |
| 5,647,873 A | 7/1997 | Errico | |
| 5,690,630 A | 11/1997 | Errico | |
| 5,817,094 A | 10/1998 | Errico | |
| 5,863,293 A | 1/1999 | Richelsoph | |
| 5,964,760 A | 10/1999 | Richelsoph | |
| 6,010,503 A | 1/2000 | Richelsoph | |
| 6,355,040 B1 | 3/2002 | Richelsoph | |
| 6,440,137 B1 | 8/2002 | Horvath et al. | |
| 6,443,953 B1 | 9/2002 | Perra et al. | |
| 6,471,705 B1 | 10/2002 | Biedermann et al. | |
| 6,520,963 B1 | 2/2003 | McKinley | |
| 6,565,565 B1 | 5/2003 | Yuan et al. | |
| 6,695,843 B2 | 2/2004 | Biedermann et al. | |
| 6,726,687 B2 * | 4/2004 | Jackson | ........................ 606/916 |
| 6,740,086 B2 | 5/2004 | Richelsoph | |
| 6,755,829 B1 | 6/2004 | Bono et al. | |
| 6,843,791 B2 | 1/2005 | Surham | |
| 6,918,911 B2 * | 7/2005 | Biedermann et al. | ......... 606/267 |
| 7,204,838 B2 * | 4/2007 | Jackson | ........................ 606/270 |
| 7,335,202 B2 * | 2/2008 | Matthis et al. | ................. 606/266 |
| 2002/0082602 A1 | 6/2002 | Biedermann et al. | |
| 2003/0023240 A1 * | 1/2003 | Amrein et al. | ................... 606/61 |
| 2004/0138662 A1 | 7/2004 | Landry et al. | |
| 2004/0147937 A1 | 7/2004 | Dunbar | |
| 2004/0172022 A1 | 9/2004 | Landry et al. | |
| 2004/0186473 A1 * | 9/2004 | Cournoyer et al. | ............. 606/61 |
| 2004/0193160 A1 | 9/2004 | Richelsoph | |
| 2005/0149036 A1 | 7/2005 | Varieur | |
| 2005/0154389 A1 | 7/2005 | Selover et al. | |
| 2005/0216000 A1 * | 9/2005 | Colleran et al. | ................ 606/61 |
| 2006/0074418 A1 | 4/2006 | Jackson | |

FOREIGN PATENT DOCUMENTS

| | | |
|---|---|---|
| EP | 1 269 930 | 1/2003 |
| EP | 1 374 786 | 1/2004 |

OTHER PUBLICATIONS

PCT search report for PCT/US2007/065913.
Written Opinion for PCT/US2007/065913.

\* cited by examiner

*Primary Examiner* — Thomas C Barrett
*Assistant Examiner* — Michael J Araj

(57) ABSTRACT

A device for reducing stabilization into a head of a medical implant is provided. The device includes a rotating member and a ram for reducing the stabilization member into a core of the implant head. The ram is threadably engaged with the rotating member and is moved by rotation of the rotating member.

23 Claims, 6 Drawing Sheets

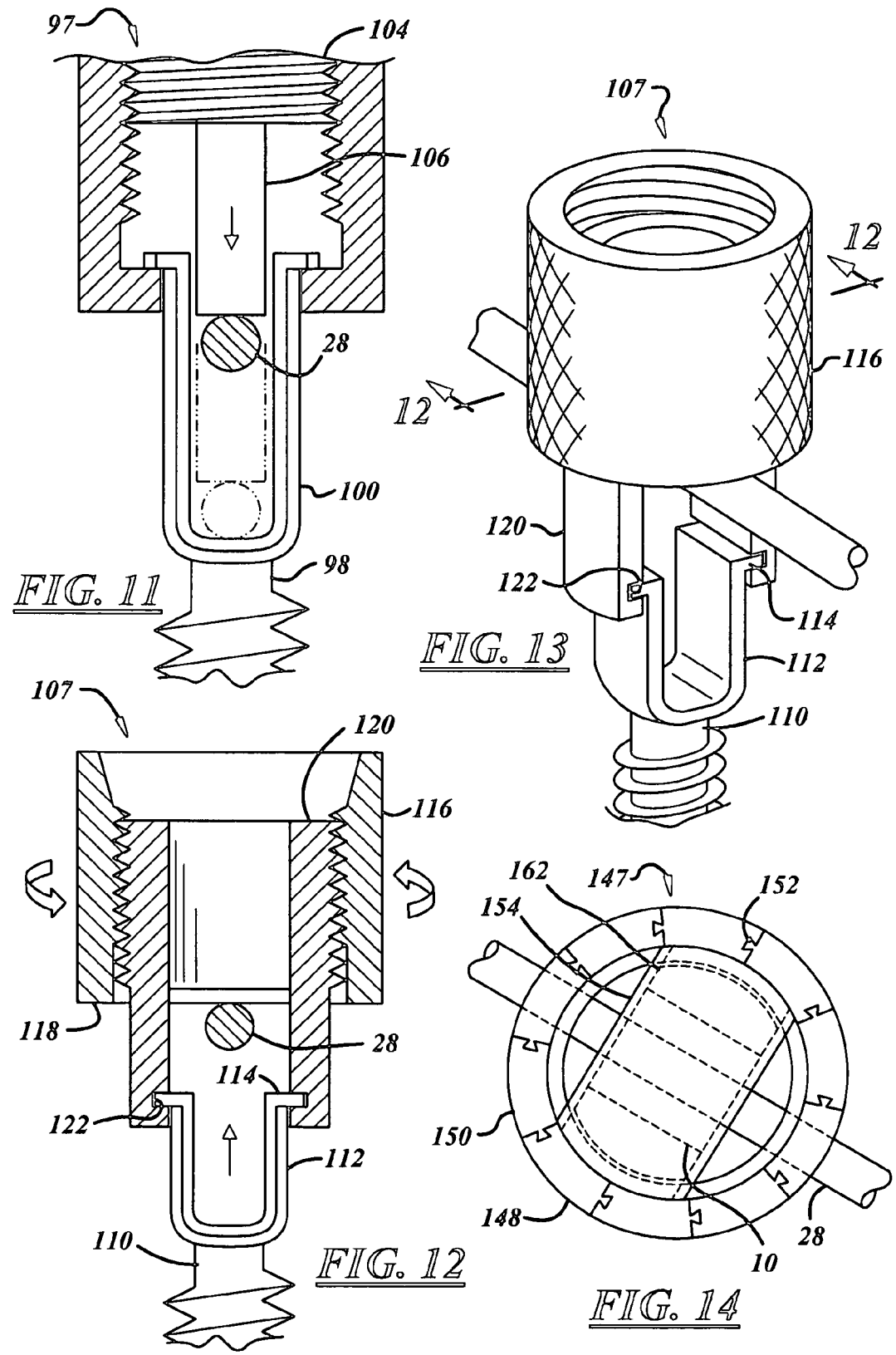

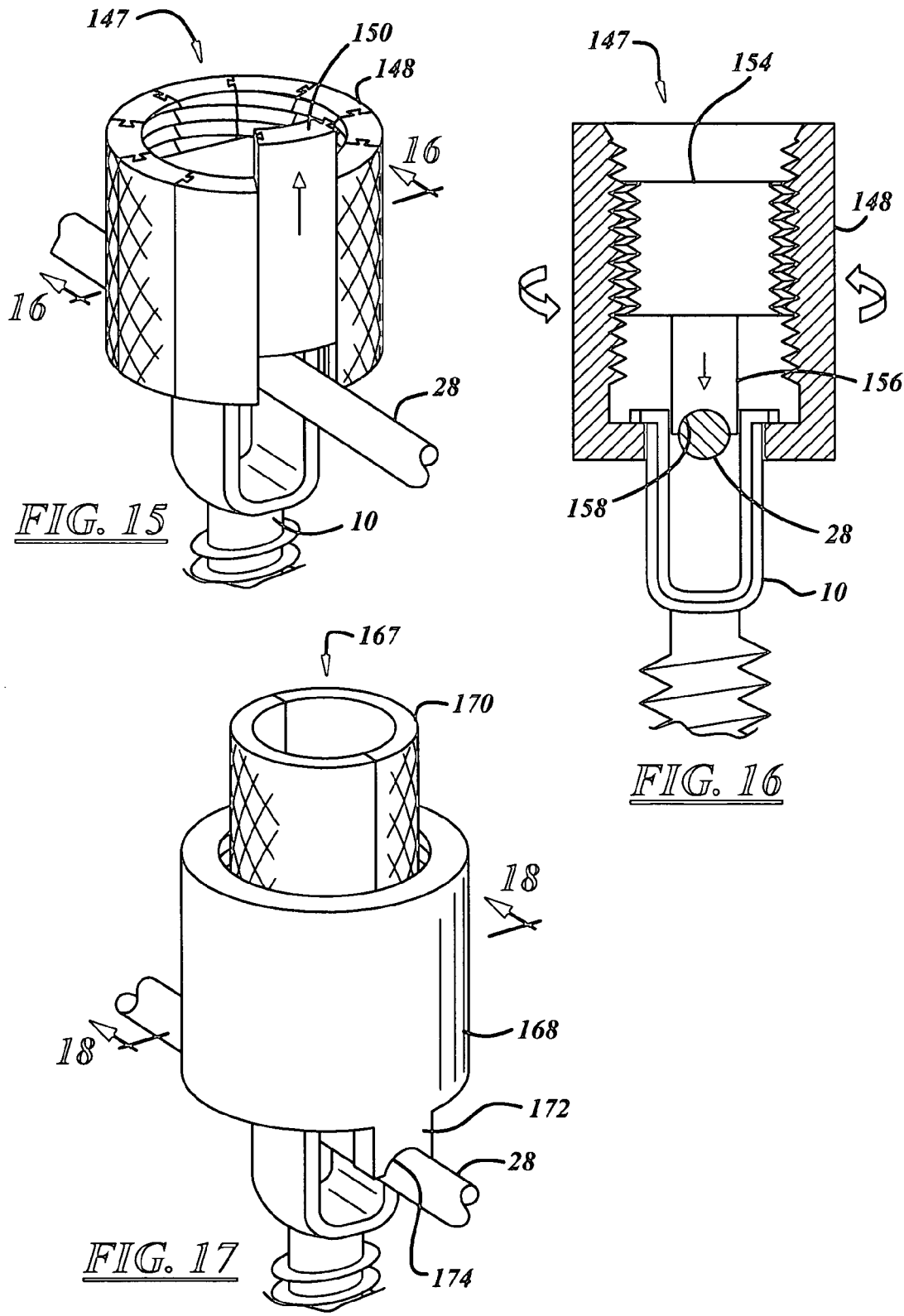

REDUCING DEVICE

FIELD OF THE INVENTION

The present invention relates to reducing devices used for reducing stabilization members such as rods or plates into medical implants such as pedicle screws or spinal hooks.

BACKGROUND OF THE INVENTION

Spinal surgeons often treat spinal disorders with spinal fusion augmented with stabilization members such as plates or elongated spinal rods connected to the spine with implants such as pedicle screws or spinal hooks. Such "stabilization assemblies" often comprise one or two spinal rods or plates and a plurality of implants engaging the pedicles of their respective vertebral bodies. The implants are provided with U-shaped heads that can be capped to couple the stabilization members to the implants. During the surgical procedure to couple the stabilization member to the implants, it is often necessary to use a tool or device to push or "reduce" the stabilization member onto the implant heads. It is desirable that such a device offer the surgeon a significant mechanical advantage in the reduction procedure.

SUMMARY OF THE INVENTION

To make manifest the above noted and other manifold desires, a revelation of the present invention is brought forth. The present invention provides a device for reducing a stabilization member into a head of a medical implant. The device includes a rotating member and a ram for reducing the stabilization member into a core of the implant head. The ram is threadably engaged with the rotating member and is moved by rotation of the rotating member.

Other features of the invention will become more apparent to those skilled in the art as the invention is further revealed in the accompanying drawings and Detailed Description of the Invention.

BRIEF DESCRIPTION OF THE DRAWINGS

FIG. 11 is a sectional view of another alternate preferred embodiment reducing device of the present invention.

FIG. 12 is a view taken along line 12-12 of FIG. 13.

FIG. 13 is a perspective view of another alternate preferred embodiment reducing device of the present invention.

FIGS. 14, 15 and 16 are top plan, perspective, and sectional views respectively of another alternate preferred embodiment reducing device of the present invention.

FIGS. 17, 18 and 19 are perspective, partially exploded and sectional views respectively of yet another alternate preferred embodiment reducing device of the present invention.

DETAILED DESCRIPTION OF THE INVENTION

Figure 1:
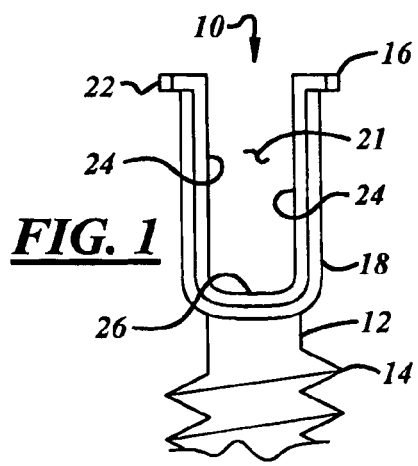
FIG. 1 is a partial enlarged front elevation view of a screw implant utilized with a reducing device of the present invention.
Figure 2:
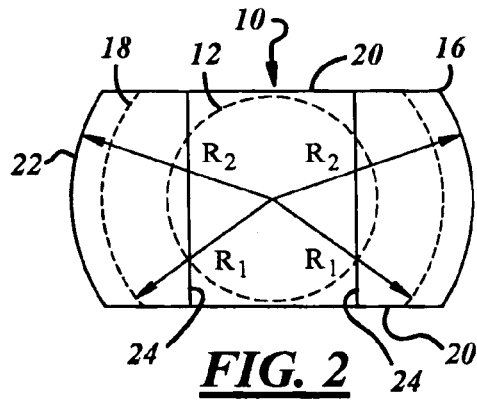
FIG. 2 is a top plan view of the screw shown in FIG. 1.
Figure 4:
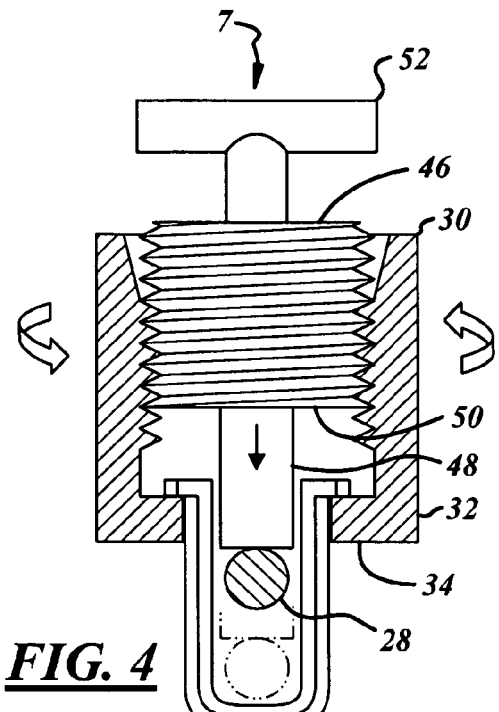
FIG. 4 is a sectional view of the reducing device shown in FIG. 3.

Referring to FIGS. 1, 2 and 4, a device 7 for reducing a stabilization member such as a rod or plate into a head of an implant such as a spinal hook or a pedicle screw is provided. Typically, the screw 10 has a shank 12 with a bone engaging portion 14. The screw 10 typically is inserted into a bone structure of a patient. As shown the pedicle screw 10 on top of the shank 12 has a head 16. The head 16 is generally U-shaped. As best shown in FIGS. 1 and 2, the screw head 16 has a main body 18 with a radius R1. The body 18 has front and rear chordal flats 20. The body 18 also has circular shaped protrusions 22 with a radius R2. The head 16 also has a central core 21 defined by generally parallels side walls 24 and a floor 26. In certain types of the spinal surgeries a series of screws 10 are inserted into the vertebrate pedicles of the patient spine. The screws 10 are connected with an elongated rod 28 to maintain their position and alignment. Often the rod 28 will have to be pushed in to a head 16 of the screw. The above noted process is often referred to as reducing the rod into the screw.

The reducing device 7 has a driver or rotating member 30. The rotating member 30 has an extreme end 32. The rotating member extreme end 32 has a radially inward projecting flange 34. The flange 34 typically interfaces in a non-threaded manner with the screw head 16 underneath the protrusions 22. Threadably engaged with the rotating member 30 is a ram 46. The ram 46 has an engagement head 48. The engagement head 48 connects with an upper portion exterior threaded body 50. Connected on top of the ram body 50 is an anti-rotational handle 52.

The surgeon will rotate the rotating member 30 as shown in FIG. 4. The rotation of the rotating member 30 moves ram 46 downward causing the ram head 48 to push the rod 28 toward the screw head floor 26. The surgeon can use one of their hands to hold the handle 52 to keep the ram 48 from rotating with the rotating member 30. As the rod 28 is reduced in another screw (not shown), a rod locking cap is connected with the screw head to hold down the rod 28 within the screw head. The screw head body 18 may be threaded along a partial interior circumference (not shown) or along a circumferential surface of the screw head protrusions 22 for threaded connection with a locking cap. In other embodiments (not shown), the locking cap may be connected by crimping or an interference fit.

To allow the flange 34 to get under the protrusions 22, the rotating member 30 has two halves 36 (FIGS. 5 and 6) that are joined in a clamshell manner by a pair of hinge pins 38 (only one shown). Each rotating member half 36 has a threaded portion 44. The rotating member halves 36 open up to allow the flanges 34 to interface with the screw head 16 underneath the protrusions 22 upon closure. A top end of the rotating member's halves 36 has a taper 42 along the interior diameter. The taper 42 allows the halves 36 to open up without interfering with the screw threads 49 of the ram. The taper 42 also accommodates the threaded insertion of the ram 46 into the rotating sleeve 30. To release the reducing device 7 form a given screw, the halves 36 of the rotating member are opened and the reducing device 7 is optionally be used another screw 10 that is being connected with the rod 28

Figure 8A:
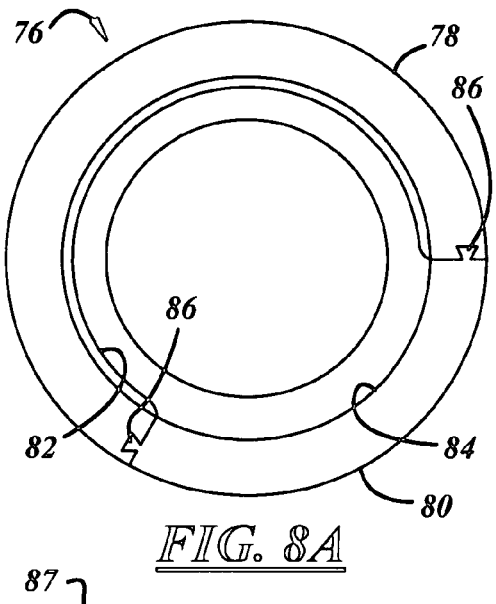
FIG. 8A is a top plan view of the rotating member shown in FIG. 8.
Figure 8:
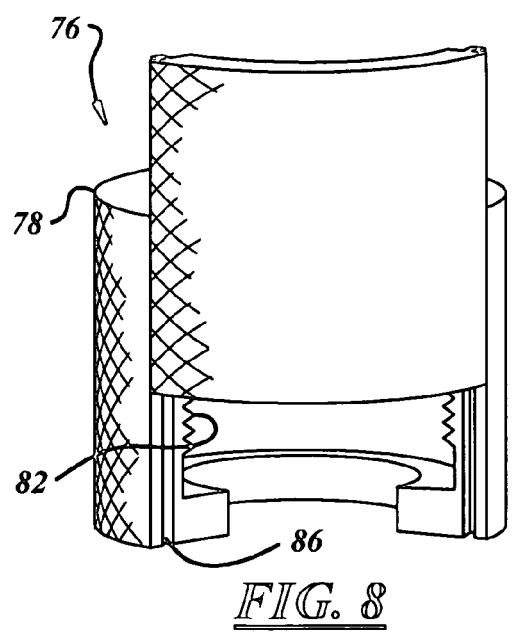
FIG. 8 is a perspective view of a rotating member that can be utilized with the reducing device shown in FIG. 3.

FIGS. 8 and 8A provides an alternative embodiment rotating member 76 that can be used with the reducing device 7. The rotating member 76 has a cylindrical large sleeve 78 and a cylindrical small sleeve 80. The large sleeve 78 has interior threads 82. The small sleeve 80 has a generally smooth interior diameter 84. The small sleeve 80 has tongue and groove connections 86 with the large sleeve 78. To allow the flange of the rotating member 76 to encircle the screw head 16, the small sleeve 80 is moved up providing an access slot. A smooth interior diameter 84 of the small sleeve prevents interfere with the threaded body 50 of the ram.

Figure 7:
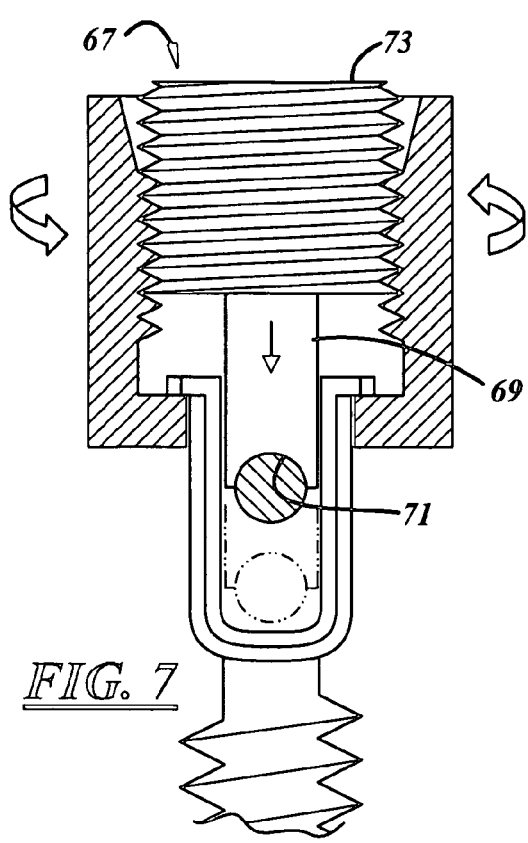
FIG. 7 is a sectional view of an alternate preferred embodiment reducing device of the present invention.

Referring back to FIG. 7, an alternate preferred embodiment reducing device 67 is provided. The reducing device 67 has a ram head 69. The ram head 69 has an intention 71 allowing it to engage the rod 28. With the reduction device 67, the ram 73 is prevented from rotation by virtue of the rod engagement. The ram handle can be eliminated or optionally be provided for the ease of handling the reduction device 67.

Figure 5:
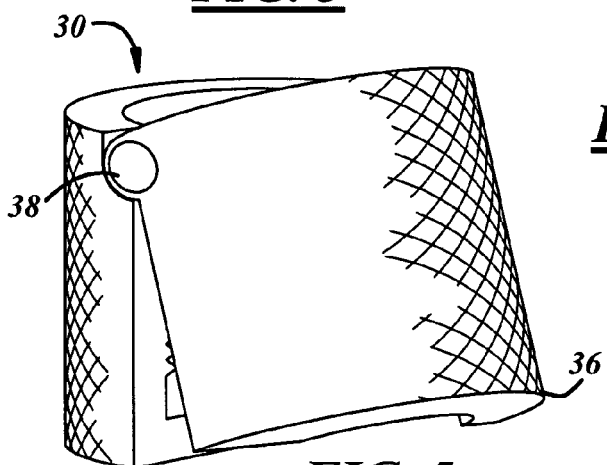
FIGS. 5 and 6 are perspective and sectional views of a rotating member utilized in the reducing device shown in FIG. 3.
Figure 6:
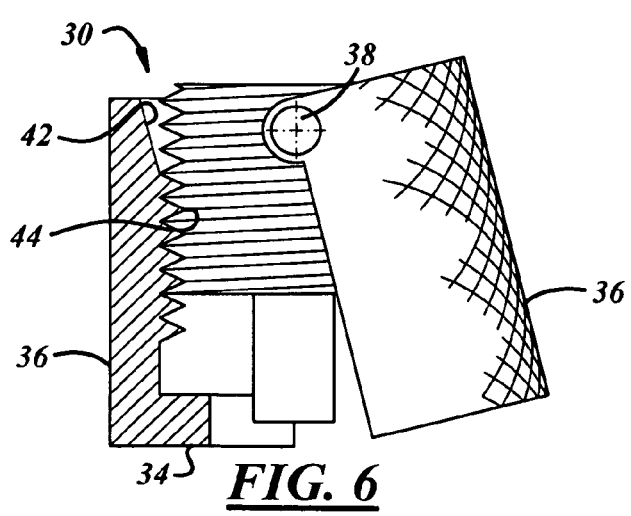
Figure 9:
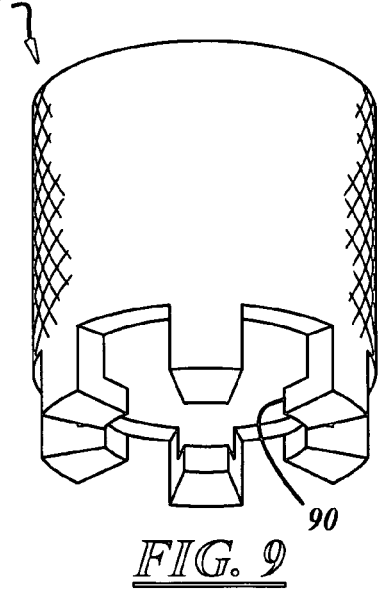
FIG. 9 is a perspective view of a rotating member that can be utilized with the reducing device shown in FIG. 3.
Figure 10:
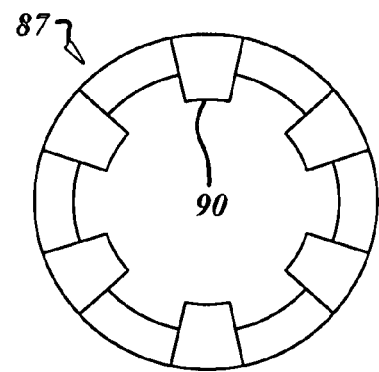
FIG. 10 is a bottom view of the rotating member shown in FIG. 9.

Referring to FIGS. 9 and 10, another alternate preferred embodiment rotating member 87 is provided. Instead of the continuous flange of 34 of the prior described rotating members, the rotating member 87 has a geometrically spaced series of radially inward projecting fingers 90 which provide point contact underneath the projections 22. The rotating member 87 can be hinged as shown in FIGS. 5 and 6 or have a sliding sleeve providing an access slot as shown in FIGS. 8 and 8A.

Referring to FIG. 11, an alternate preferred embodiment reducing device 97 is provided. A medical screw 98 has an elongated head 100 that is at least 2.5 times the diameter of the rod 28. To facilitate reducing the rod 28 into the elongated head 100, the ram 104 is provided with an elongated head 106.

Referring to FIGS. 12 and 13, an alternate preferred embodiment reducing device 107 shown. A medical screw 110 provided that has a U-shaped channel head 112 with rectangular protrusions 114. The reducing device 107 is best utilized in situations as shown in FIGS. 12 and 13 wherein the rod 28 is in a position far above the head 112 of the screw 110. The reducing device 107 has a rotating member 116. The rotating member 116 has a lower edge 118 that acts as a vertical stop for the rod 28. A ram 120 has rectangular grooves 122 that interface with the protrusions 114 of the screw 110. Accordingly, the ram 120 is prevented from rotation. Tourqing of the rotating member 116 causes the screw 110 to be pulled urged.

Referring to FIGS. 14-16 an alternate preferred embodiment reducing device 147 is provided. Again, the reducing device 147 is best utilized in an environment wherein the rod 28 is positioned well above the screw 10. A rotating member 148 has a plurality of movable sleeves 150 that are held together by tongue and groove connections 152. A ram 154 has a head 156 with an indent 158 to prevent the ram from rotation. (Other embodiments the ram, not shown can be supplied with a handle as previously described). The ram 154 has a body with radial ends 162. The radial ends 162 are threadably engaged with one or two of the sleeves 152. As a sleeve 150 approaches the rod 28, the interfering sleeve 150 is raised to provide clearance. Once past the rod, the previously raised sleeve is moved back down. The interfering sleeve 150 is free to move upward or downward since it is not engage with one of the radial ends 162 of the ram.

Figure 18:
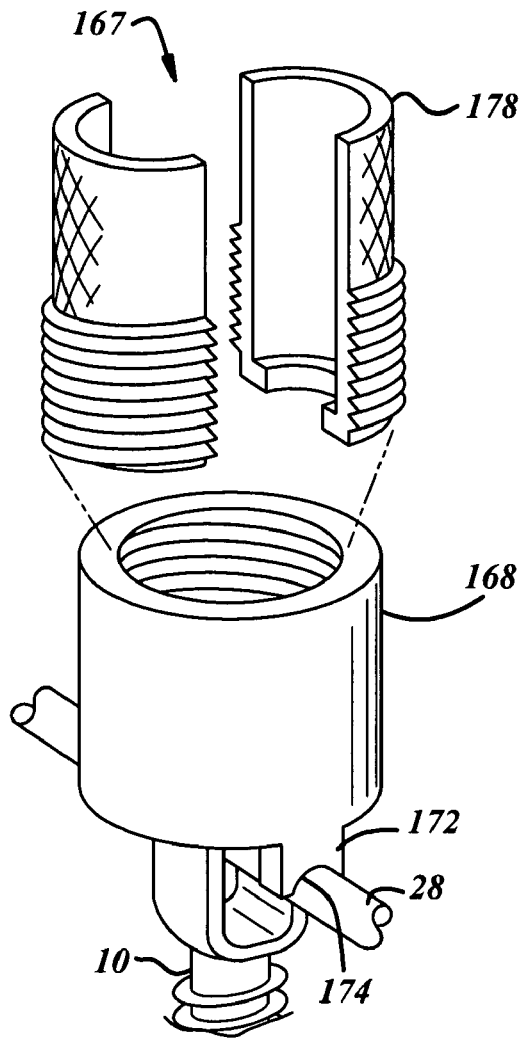
Figure 19:
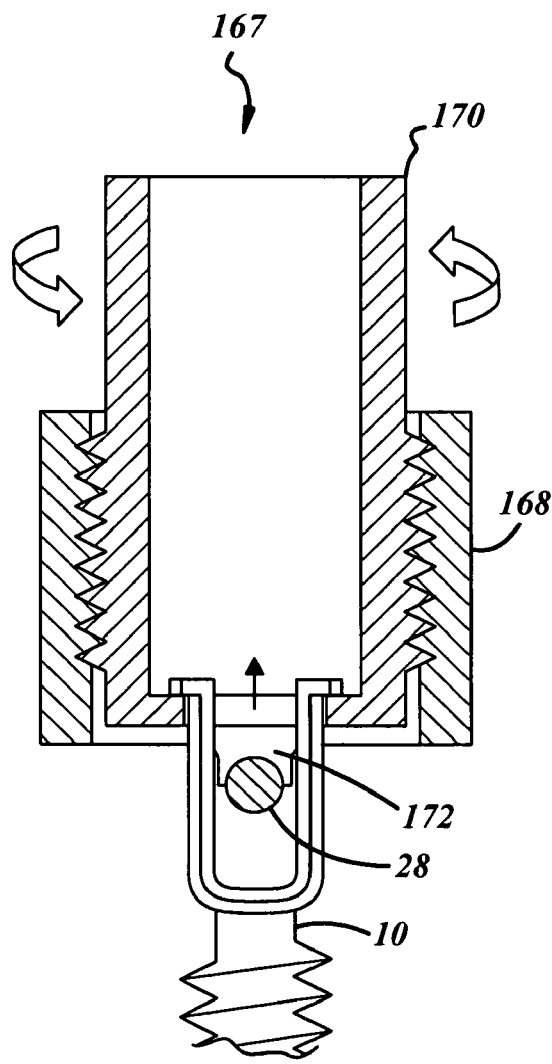

Referring to FIGS. 17-19, an alternate preferred embodiment reducing device 167 is provided. The reducing device 167 has a ram 168 threadably engaged with a rotating member 170 along the rams interior. The ram 168 has a head 172 with an intention 174 to non-rotatably engaged with a rod for rotational restraint of the ram 168. The rotating member 170 has separable halves 178 that allow a surgeon to position them with their flange underneath the protrusions 22 of the screw 10. The ram 168 can then be threaded onto the rotating member 170 to a position placing the indention 174 in alignment with the rod 28. Subsequent rotation of the rotating member 170 will force the ram 168 downward reducing the rod 28 into the head of the screw 10.

Figure 2A:
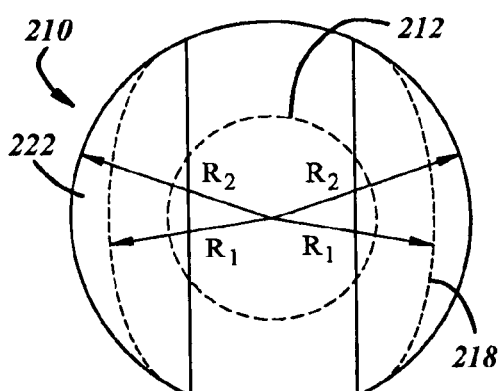
FIG. 2A is a top plan view of an alternate embodiment screw, which can be utilized, with the reducing device of the present invention.

Referring to FIG. 2A, an alternative embodiment screw 210 is provided. The screw 210 has a shank 212 substantially similar to the screw shank 12 as previously described. The shank 212 is connected to a head. The head 216 has an oval cross-sectional shaped body 218. Crescent shaped protrusions 222 extend from opposite sides of the body 218. The protrusions 222 have a generally fixed outer radius of R2 and a variable radius R1. The head has a central core with parallel spaced side walls 224. The screw 212 is best utilized with the reducing instruments wherein the rotating member is presented in separable halves.

Figure 2B:
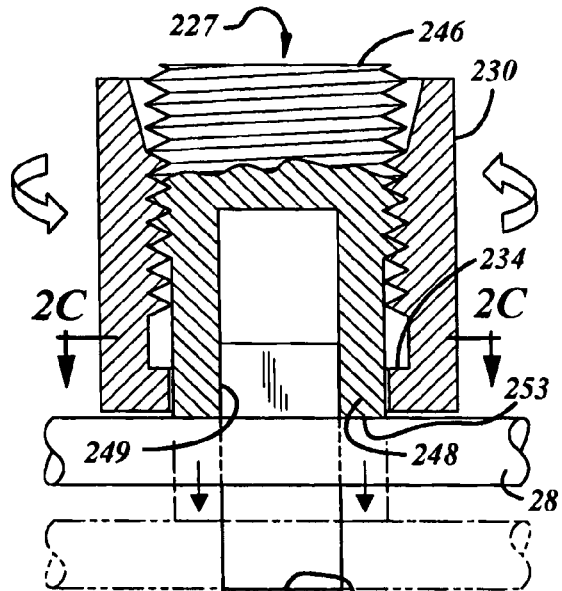
FIG. 2B is a sectional view of an alternate preferred embodiment reducing device of the present invention.
Figure 2C:
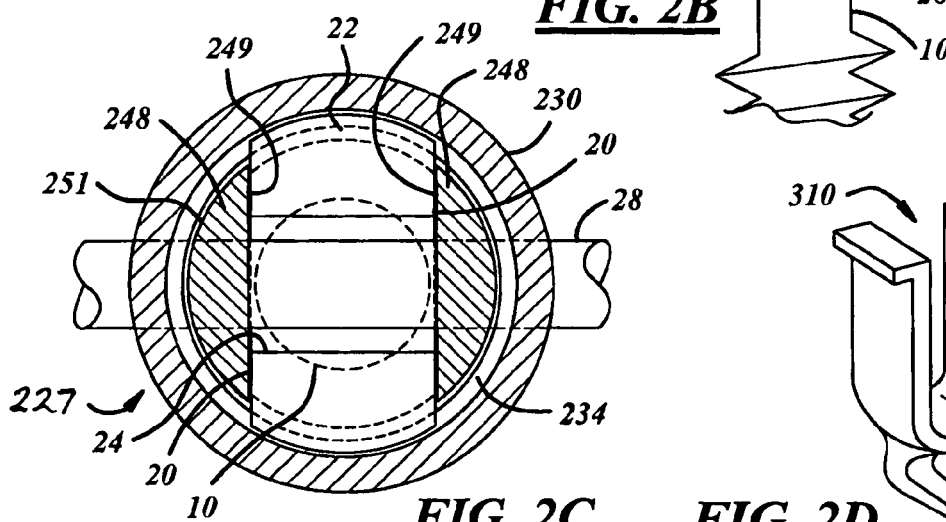
FIG. 2C is a view taken along line 2C-2C of FIG. 2B.

Referring back to FIGS. 2B and 2C an alternate preferred embodiment reducing device 227 is provided. The reducing the device 227 can have a rotating member 230 substantially similar to the rotating members 30 or 76 previously described. The rotating member 230 has a shortened inwardly directed flange 234. A ram 246 is provided having spaced apart dual engagement heads 248. Each engagement head 248 has a flat 249 that slideably mates and aligns with the chordal flats 20 of the screw 10. The engagement heads 248 have an outer diameter 251 providing it with a slight clearance with the rotating member flange 234. The protrusions 22 of the screw ride on top of the flange 234. Rotation of the rotating member 230 causes the ram 246 to be urged downward. The flats 249 of the dual engagement heads 248 aligned with the chordal flats 20 of the screw to prevent rotation of the ram 246. Bottom ends 253 of the engagement heads 248 contact the rod 28 to push it towards the screw head floor 26.

Figure 2D:
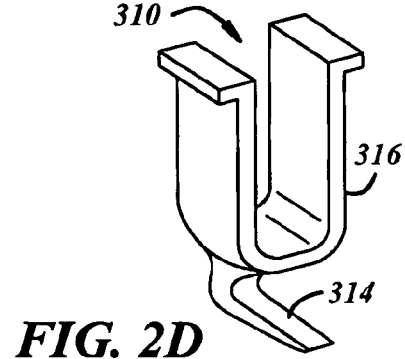
FIG. 2D is a perspective view of a spinal hook implant, which can be utilized with the reducing instrument of the present invention.
Figure 3:
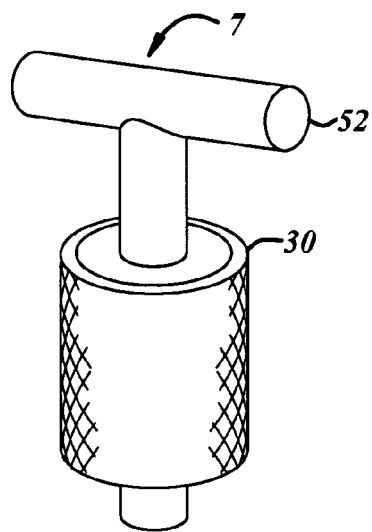
FIG. 3 is a perspective view of a preferred embodiment reducing device of the present invention.

FIG. 2D provides a spinal hook 310 having an engagement portion 314 connected with a head 316. They head 316 can be similar or identical to the implant heads previously described. A rod 28 can be reduced into the head 316 utilizing the reduction instruments described previously While preferred embodiments of the present invention have been disclosed primarily with the use pedicle screws and rod stabilization members, it is to be understood it has been described by way of example only and that other implants and stabilization members can also be utilized, and that various other modifications can be made to the present invention without departing from the spirit and scope of the invention as it is encompassed in the following claims.

The invention claimed is:

1. A device for reducing a rod into a head of an implant, said device comprising:
   an implant having a bone engaging portion connected with
      a generally U-shaped head having a core including a
      generally U-shaped channel extending transversely
      therethrough and defined by generally parallel side walls and a bottom wall, said U-shaped channel sized and configured for receiving said rod;
a rotating member rotatably engaged with the head of the implant in a non-threaded manner; and
a ram for reducing said rod into said U-shaped channel of said implant head core, said ram being threadably engaged with said rotating member while being restrained from rotation and being moved by rotation of said rotating member.

2. A device as described in claim 1 wherein said ram is internally threaded with said rotating member.

3. A device as described in claim 1 wherein said ram is externally threaded with said rotating member.

4. A device as described in claim 1, further comprising a rod positioned within said generally U-shaped channel; and
wherein said ram is prevented from rotation by engagement with said rod.

5. A device as described in claim 1 wherein said ram is prevented from rotation by engagement with said implant.

6. A device as described in claim 1 wherein said head has outwardly extending protrusions extending outwardly from said side walls, and said rotating member has an end including an inwardly extending flange interfaced with said outwardly extending protrusions.

7. A device as described in claim 6 wherein said protrusions are circular shaped.

8. A device as described in claim 1 wherein said rotating member has a removable sleeve.

9. A device as described in claim 1 wherein said ram has a handle.

10. A device as described in claim 1 wherein said rotating member has separable portions.

11. A device as described in claim 10 wherein said separable portions are hinged.

12. A device as described in claim 1, further comprising an elongate spinal rod positioned within said U-shaped channel of said implant; and
wherein said ram includes a distal engagement head positioned within an interior region of said U-shaped channel of said head and engaged in contact with said spinal rod to reduce said spinal rod along said U-shaped channel.

13. A device as described in claim 1, wherein said head includes threads formed along said generally parallel side walls; and
wherein said implant further comprises a locking cap threadedly engaged with said threads formed along said generally parallel side walls to capture said rod within said U-shaped channel.

14. A device as described in claim 1, wherein said head of said implant includes front and rear flattened end surfaces to which said generally U-shaped channel extend.

15. A method for reducing a stabilization member into a head of a medical implant, said implant having a bone engaging portion connected with a head having a core for receiving said stabilization member, said method comprising:
providing a rotating member;
threadably engaging a ram with said rotating member;
torquing said rotating member to rotate said rotating member relative to said implant head to threadedly engage the rotating member along said ram while rotatively restraining said ram to prevent rotation of said ram to thereby move said ram to reduce said stabilization member into said implant head.

16. A method for reducing a stabilization member into a head of a medical implant as described in claim 15 wherein said ram is internally threadably engaging with said rotating member.

17. A method for reducing a stabilization member into a head of a medical implant as described in claim 15 wherein said ram is externally threadably engaging with said rotating member.

18. A method for reducing a stabilization member into a head of a medical implant as described in claim 15 wherein said ram is torsionally restrained by engaging said stabilization member.

19. A method for reducing a stabilization member into a head of a medical implant as described in claim 15 wherein a handle torsionally restrains said ram.

20. A method for reducing a stabilization member into a head of a medical implant as described in claim 15, further comprising:
providing an implant having a bone engaging portion connected with a generally U-shaped head including a generally U-shaped channel extending transversely therethrough;
rotatably engaging said rotating member with said U-shaped head of said implant in a non-threaded manner with said rotating member freely rotating about said implant head as said stabilization member is reduced into said implant head;
positioning an elongate spinal rod within said generally U-shaped channel; and
wherein said torquing said rotating member while rotatively restraining said ram results in engaging said ram with said elongate spinal rod and displacing said elongate spinal rod along said generally U-shaped channel.

21. A method for reducing a stabilization member into a head of a medical implant as described in claim 15, further comprising rotatably engaging said rotating member with said head of said implant in a non-threaded manner such that said rotating member freely rotates about said implant head to reduce said stabilization member into said implant head.

22. A device for reducing a rod into a head of an implant, said device comprising:
an implant having a bone engaging portion connected with a generally U-shaped head having a core including a generally U-shaped channel extending transversely therethrough and defined by generally parallel side walls and a bottom wall, said U-shaped channel sized and configured for receiving said rod;
a rotating member rotatably engaged with the head of the implant in a non-threaded manner; and
a ram for reducing said rod into said U-shaped channel of said implant head core, said ram being threadably engaged with said rotating member while being restrained from rotation and being moved by rotation of said rotating member, wherein said ram includes a rod engagement head positioned within said U-shaped channel of said implant and configured to engage said rod to reduce said rod along said U-shaped channel.

23. A device as described in claim 22, wherein said ram includes an upper externally threaded body threadedly engaged with said rotating member, said rod engagement head comprising a lower non-threaded stem extending from said upper externally threaded body.

* * * * *